(12) United States Patent
Decre et al.

(10) Patent No.: US 9,180,299 B2
(45) Date of Patent: Nov. 10, 2015

(54) FIRST TIME RIGHT PLACEMENT OF A DBS LEAD

(75) Inventors: Michel Marcel Jose Decre, Eindhoven (NL); Hubert Cécile François Martens, Eindhoven (NL)

(73) Assignee: Medtronic Bakken Research Center B. V., Maastricht (NL)

( * ) Notice: Subject to any disclaimer, the term of this patent is extended or adjusted under 35 U.S.C. 154(b) by 606 days.

(21) Appl. No.: 12/518,158

(22) PCT Filed: Nov. 16, 2007

(86) PCT No.: PCT/IB2007/054684
§ 371 (c)(1),
(2), (4) Date: Jun. 8, 2009

(87) PCT Pub. No.: WO2008/072125
PCT Pub. Date: Jun. 19, 2008

(65) Prior Publication Data
US 2010/0036468 A1    Feb. 11, 2010

Related U.S. Application Data

(60) Provisional application No. 60/869,789, filed on Dec. 13, 2006.

(51) Int. Cl.
*A61N 1/36* (2006.01)
*A61N 1/05* (2006.01)

(52) U.S. Cl.
CPC .......... *A61N 1/36139* (2013.01); *A61N 1/0534* (2013.01); *A61N 1/36185* (2013.01);
(Continued)

(58) Field of Classification Search
CPC ..... A61N 1/05; A61N 1/0529; A61N 1/0534; A61N 1/3605; A61N 1/3606; A61N 1/36139; A61N 1/36185
USPC .................................. 607/116, 2, 9
See application file for complete search history.

(56) References Cited

U.S. PATENT DOCUMENTS 6,011,996 A * 1/2000 Gielen et al. ................. 607/116
6,044,304 A   3/2000 Baudino
(Continued)

FOREIGN PATENT DOCUMENTS

RU   2264234 C1   11/2005
WO   0245795 A2    6/2002
(Continued)

OTHER PUBLICATIONS

Decision on Grant for Russian Patent No. 2009126608 dated Aug. 1, 2012.
(Continued)

*Primary Examiner* — Christopher A Flory
(74) *Attorney, Agent, or Firm* — Shumaker & Sieffert, P.A.

(57) ABSTRACT

The disclosure is directed to a deep brain stimulation (DBS) lead having a distal end for providing therapeutic electrical stimulation to tissue in a stimulation target area of a patient's brain, comprising an array of one or more stimulation elements and sensing elements located at the distal end of the lead; each of the one or more stimulation elements is capable of providing electrical stimulation to the brain tissue in the target area; and each of the one or more sensing elements is capable of detecting electrical signals produced by nerve cells within the brain; wherein after the first implantation of the lead into the brain along a trajectory that is pre-determined by non-surgical procedures, the array of stimulation and sensing elements is capable of facilitating the location of the target area and the determination for each of the stimulation elements of the required stimulation parameters needed to provide the therapeutic stimulation to the brain tissue in the stimulation target area, without requiring any additional implantations of the lead after the first implantation. A stimulation system including the DBS lead and a pulse generator is disclosed. Also disclosed is a method of providing therapeutic DBS to brain tissue using the lead.

12 Claims, 5 Drawing Sheets

(52) U.S. Cl.
CPC ............... *A61N 1/05* (2013.01); *A61N 1/0529* (2013.01); *A61N 1/3605* (2013.01); *A61N 1/3606* (2013.01); *A61N 1/36082* (2013.01)

(56) References Cited

U.S. PATENT DOCUMENTS

| | | | |
|---|---|---|---|
| 6,304,784 | B1 | 10/2001 | Allee et al. |
| 6,473,653 | B1 | 10/2002 | Schallhorn et al. |
| 7,177,701 | B1 * | 2/2007 | Pianca ................... 607/116 |
| 7,941,202 | B2 * | 5/2011 | Hetke et al. ............ 600/377 |
| 7,953,497 | B1 * | 5/2011 | Pianca et al. ........... 607/117 |
| 8,010,200 | B1 * | 8/2011 | Pianca ..................... 607/45 |
| 8,271,094 | B1 * | 9/2012 | Moffitt et al. .......... 607/116 |
| 2001/0016765 | A1 | 8/2001 | Gielen et al. |
| 2003/0083724 | A1 * | 5/2003 | Jog et al. ................ 607/122 |
| 2004/0199235 | A1 * | 10/2004 | Younis ................... 607/116 |
| 2005/0154414 | A1 | 7/2005 | Perreault et al. |
| 2005/0154424 | A1 | 7/2005 | Tass |
| 2005/0246004 | A1 | 11/2005 | Cameron |
| 2006/0095105 | A1 * | 5/2006 | Jog et al. ................ 607/116 |
| 2006/0149337 | A1 * | 7/2006 | John ......................... 607/45 |
| 2006/0217781 | A1 * | 9/2006 | John ......................... 607/45 |
| 2006/0265039 | A1 * | 11/2006 | Bartic et al. ............ 607/116 |
| 2006/0276866 | A1 * | 12/2006 | McCreery ............... 607/116 |
| 2007/0060974 | A1 * | 3/2007 | Lozano ..................... 607/45 |
| 2007/0129770 | A1 * | 6/2007 | Younis ..................... 607/45 |
| 2009/0326627 | A1 * | 12/2009 | Moffitt et al. .......... 607/116 |
| 2011/0307030 | A1 * | 12/2011 | John ......................... 607/45 |

FOREIGN PATENT DOCUMENTS

| | | |
|---|---|---|
| WO | 03028521 A2 | 4/2003 |
| WO | 2005113063 A1 | 12/2005 |
| WO | 2006060705 A1 | 6/2006 |

OTHER PUBLICATIONS

Examination Report from Counterpart European Patent Application No. 07849171.9, dated Dec. 8, 2014, 5 pp.

Office Action from U.S. Appl. No. 14/299,326, dated Apr. 30, 2015, 10 pp.

* cited by examiner

FIRST TIME RIGHT PLACEMENT OF A DBS LEAD

The disclosure is directed to a deep brain stimulation (DBS) lead having a distal end for providing therapeutic electrical stimulation to tissue in a stimulation target area of a patient's brain, comprising an array of one or more stimulation elements and sensing elements located at the distal end of the lead; each of the one or more stimulation elements is capable of providing electrical stimulation to the brain tissue in the target area; and each of the one or more sensing elements is capable of detecting electrical signals produced by nerve cells within the brain; wherein after the first implantation of the lead into the brain along a trajectory that is predetermined by non-surgical procedures, the array of stimulation and sensing elements is capable of facilitating the location of the target area and the determination for each of the stimulation elements of the required stimulation parameters needed to provide the therapeutic stimulation to the brain tissue in the stimulation target area, without requiring any additional implantations of the lead after the first implantation. A stimulation system including the DBS lead and a pulse generator are disclosed. Also disclosed is a method of providing therapeutic DBS to brain tissue using the lead.

Successful deep brain stimulation treatment requires an accurate placement of the stimulation electrodes within the stimulation target area. In current best practice, prior to the implantation of the chronic stimulation electrodes a major amount of time during the surgical procedure is spent on the electrophysiological exploration with micro-electrodes of the target area. This lengthy procedure extends the surgery by hours and a solution that allows the same, or better, electrophysiological mapping of the target area for stimulation is highly desired.

Following the first demonstrations of the disappearance of tremor upon electrical stimulation of thalamic targets in the late 1980s, deep brain stimulation (DBS) has become an accepted technique for the treatment of advanced Parkinson's disease. A lead carrying a number of electrodes (typically 4 circumferential electrodes, for example, as in the Medtronic DBS electrode 3389) is surgically implanted in the stimulation target, for instance the subthalamic nucleus (STN) or the globus pallidus internal segment (GPi). This lead is connected by means of extension wires to a pulse generator, which produces the electrical pulses required for the stimulation. The typical parameters for so called high-frequency DBS (HF-DBS) are pulse length 60-100 μs, pulse repetition frequency 130-185 Hz, and pulse amplitude 1.5-5 V. It is generally accepted that under these conditions HF-DBS mimics the effects of a functional lesion of the stimulation target.

An important merit of HF-DBS is its reversibility. When the electrical stimulation is interrupted its effects are fully undone. This is a clear advantage over respective surgery, which is irreversible by nature, and it allows to cease, or adjust, the treatment in case of negative outcomes. Moreover, the spatially localized delivery of the electrical stimulation is an important advantage over pharmaceutical treatments, where typically the drugs exert a global effect often leading to unwanted side-effects. Asserted by both the clinically proven efficacy of the method for Parkinson's disease and the relatively straightforward exploration of the clinical effects of this technique on other targets, researchers are now exploring new indications for the treatment. Future disorders that might be treated by HF-DBS include dystonia, epilepsy, obsessive compulsive disorder, cluster headaches, obesity, and even depression.

An important requirement for a successful outcome of the HF-DBS treatment, is the accurate placement of the stimulation electrodes within the stimulation target area. Mislocation of the electrodes is suspected to be a main cause of unwanted side-effects including sensory motor effects but also mood changes such as depression and even suicidal ideas. Through careful surgical procedures, neurosurgeons try to minimize the risks for such unwanted side-effects. The general procedure advocated by experts in the field is as follows. Prior to operation, the approximate target area is localized by means of stereotactic imaging procedures. Subsequently, an implantation trajectory is planned that bears minimal risk for damage.

Still, these methods lack the accuracy that is needed for an immediate successful positioning of the stimulation electrodes for two reasons. First, the exact functional anatomy within the target nucleus or brain region cannot yet be captured by imaging, as it often spans just a few mm, or even less, within the total nucleus or region. Second, position changes in the brain may occur when surgically opening the skull to implant the electrodes and when inserting the electrodes. The current best practice, therefore, is to perform prior to implantation of chronic stimulation electrodes an electrophysiological exploration of the target area with test electrodes that are implanted along several parallel trajectories towards the target area, capturing a sufficiently large scan volume to guarantee that the optimal stimulation target area is located in the sampled volume of tissue. Micro-recordings of the neural firing patterns are performed to explore the detailed functional boundaries of the various anatomic structures. Test stimulation is performed to assess the efficacy of the stimulation at various candidate locations. Only after the micro-recordings and test-stimulation have uncovered the precise location of the stimulation target area, the chronic stimulation electrodes are implanted.

Although indispensable for successful surgery, the electrophysiological exploration of the HF-DBS target area brings with it severe disadvantages. First, the operation time is extended by several hours leading to increased burden for the patient (who is awake during surgery) as well as heightened costs of the procedure. Second, the multiple implantation trajectories of the test electrodes and the subsequent final implantation of the chronic electrodes raises the risks of hitting a blood vessel leading to hemorrhage.

Therefore, there is a need for an improved DBS lead system and method that allows a first time, direct and accurate placement by implantation of the stimulation electrodes within the stimulation target area, which the herein disclosed methodology and system satisfies.

According to the present disclosure, a deep brain stimulation (DBS) lead and method for providing therapeutic electrical stimulation to tissue in a stimulation target area of a patient's brain is disclosed, which is capable of facilitating the location of the target area and the determination for each of the stimulation elements of the required stimulation parameters needed to provide the therapeutic stimulation to the brain tissue in the stimulation target area, without requiring any additional implantations of the lead after the first implantation.

Specifically, it is an object of this invention to provide a deep brain stimulation lead having a distal end for providing therapeutic electrical stimulation to tissue in a stimulation target area of a patient's brain, comprising:

an array of one or more stimulation elements and one or more sensing elements located at the distal end of the lead;

each of the one or more stimulation elements is capable of providing electrical stimulation to the brain tissue in the target area; and each of the one or more sensing elements is capable of detecting electrical signals produced by nerve cells within the brain;

wherein after the first implantation of the lead into the brain along a trajectory that is pre-determined by non-surgical procedures, the array of stimulation and sensing elements is capable of facilitating the location of the target area and the determination for each of the stimulation elements of the required stimulation parameters needed to provide the therapeutic stimulation to the brain tissue in the stimulation target area, without requiring any additional implantations of the lead after the first implantation.

Another object is to provide a stimulation lead wherein the stimulation elements are metal electrodes.

Another object is to provide a stimulation lead wherein the sensing elements are metal micro-electrodes or capacitive sensing elements.

Another object is to provide a stimulation lead wherein the one or more stimulation elements and the one or more sensing elements are distributed in an array circumferentially on the surface of the lead in the proximity of the distal end of the lead.

Another object is to provide a stimulation lead wherein the sensing elements are each individually capable of detecting one or more of electrical signals, action potentials, field potentials, biochemical signals and neurotransmitters.

Another object is to provide a stimulation lead wherein the area of a single sensing element is smaller than the area of a single stimulation element.

Another object is to provide a stimulation lead wherein a plurality of sensing elements are electrically combined to detect a single electrical signal.

Another object is to provide a stimulation lead wherein the number of sensing elements is larger than the number of stimulation elements.

Another object is to provide a stimulation lead wherein the stimulation parameters are selected from one or more of stimulation amplitude, polarity, duration repetition frequency, waveform, and relative phase within the stimulation duty cycle.

Another object is to provide a stimulation lead wherein the lead further comprises a controller for receiving signals from the one or more sensing elements, for determining the location of the target area and for determining which of the stimulation elements is located in or near the target area and that should be selected to provide the therapeutic stimulation to the brain tissue in the target area.

Another object is to provide a stimulation lead wherein the controller is capable of determining for each of the selected stimulation elements the required stimulation parameters needed to provide the therapeutic stimulation to the brain tissue in the target area.

Another object is to provide a stimulation lead wherein the controller is capable of using the signals received from one or more specific sensing elements to control relative stimulation amplitudes and/or timings of one or more specific stimulating elements.

Another object is to provide a stimulation system for providing after implantation therapeutic electrical stimulation to tissue in a stimulation target area of a patient's brain, comprising:

a pulse generator for generating and transmitting electrical pulses required for the stimulation; and a deep brain stimulation lead having a distal end for providing after implantation therapeutic electrical stimulation to tissue in a stimulation target area of a patient's brain, comprising:

an array of one or more stimulation elements and one or more sensing elements located at the distal end of the lead;

each of the one or more stimulation elements is capable of providing electrical stimulation to the brain tissue in the target area; and each of the one or more sensing elements is capable of detecting electrical signals produced by nerve cells within the brain;

wherein after the first implantation of the lead into the brain along a trajectory that is pre-determined by non-surgical procedures, the array of stimulation and sensing elements is capable of facilitating the location of the target area, the association and/or selection of stimulation elements in or near the target area, and the determination for each of the selected stimulation elements of the required stimulation parameters needed to provide the therapeutic stimulation to the brain tissue in the stimulation target area, without requiring any additional implantations of the lead after the first implantation.

Another object is to provide a method of providing therapeutic deep brain electrical stimulation to tissue in a stimulation target area of a patient's brain, comprising:

determining by non-surgical imaging procedures the approximate target area for stimulation and the trajectory for implantation of a deep brain stimulation lead into the approximate target area;

implanting along the trajectory and into the approximate target area the deep brain stimulation lead, the stimulation lead comprising:

an array of one or more stimulation elements and one or more sensing elements located at the distal end of the lead;

each of the one or more stimulation elements is capable of providing electrical stimulation to the brain tissue in the target area; and each of the one or more sensing elements is capable of detecting electrical signals produced by nerve cells within the brain; wherein after the first implantation of the lead into the brain along a trajectory that is pre-determined by non-surgical procedures, the array of stimulation and sensing elements is capable of facilitating the location of the target area, the association and/or selection of stimulation elements in or near the target area, and the determination for each of the selected stimulation elements of the required stimulation parameters needed to provide the therapeutic stimulation to the brain tissue in the stimulation target area, without requiring any additional implantations of the lead after the first implantation;

detecting by the one or more sensing elements of the electrical signals produced by nerve cells within the brain;

determining from the detected electrical signals produced by nerve cells within the brain the three dimensional spatial location and boundary of the stimulation target area within the approximate target area;

determining which of the one or more specific stimulation elements will be selected to provide stimulation to the brain tissue within the stimulation target area and the specific stimulation parameters for each of the one or more selected stimulation elements to be used during the stimulation; and performing stimulation of the tissue within the stimulation target area of the brain with the selected stimulation elements using the specific stimulation parameters for each of the selected stimulation elements.

Another object is to provide a method wherein the detecting by the one or more sensing elements of the electrical signals produced by nerve cells within the brain, further comprises:

reading out the electrical signal characteristics of the nerve cells within the brain detected by the one or more sensing elements; and determining the specific sensing elements that detect the signal characteristics that correspond to the stimulation target area.

Another object is to provide a method further comprising prior to the step of performing the stimulation of the brain tissue:

testing the stimulation target area by delivering test electrical stimulation by the selected one or more stimulation elements to the brain tissue in the stimulation target area and repeating the steps of the method as needed until confirmation of a functionally efficient stimulation target area is obtained.

Another object is to provide a method wherein the stimulation parameters are selected from one or more of stimulation amplitude, polarity, duration repetition frequency, waveform, and relative phase within the stimulation duty cycle.

These and other aspects of the invention are explained in more detail with reference to the following embodiments and with reference to the figures.

Figure 1:
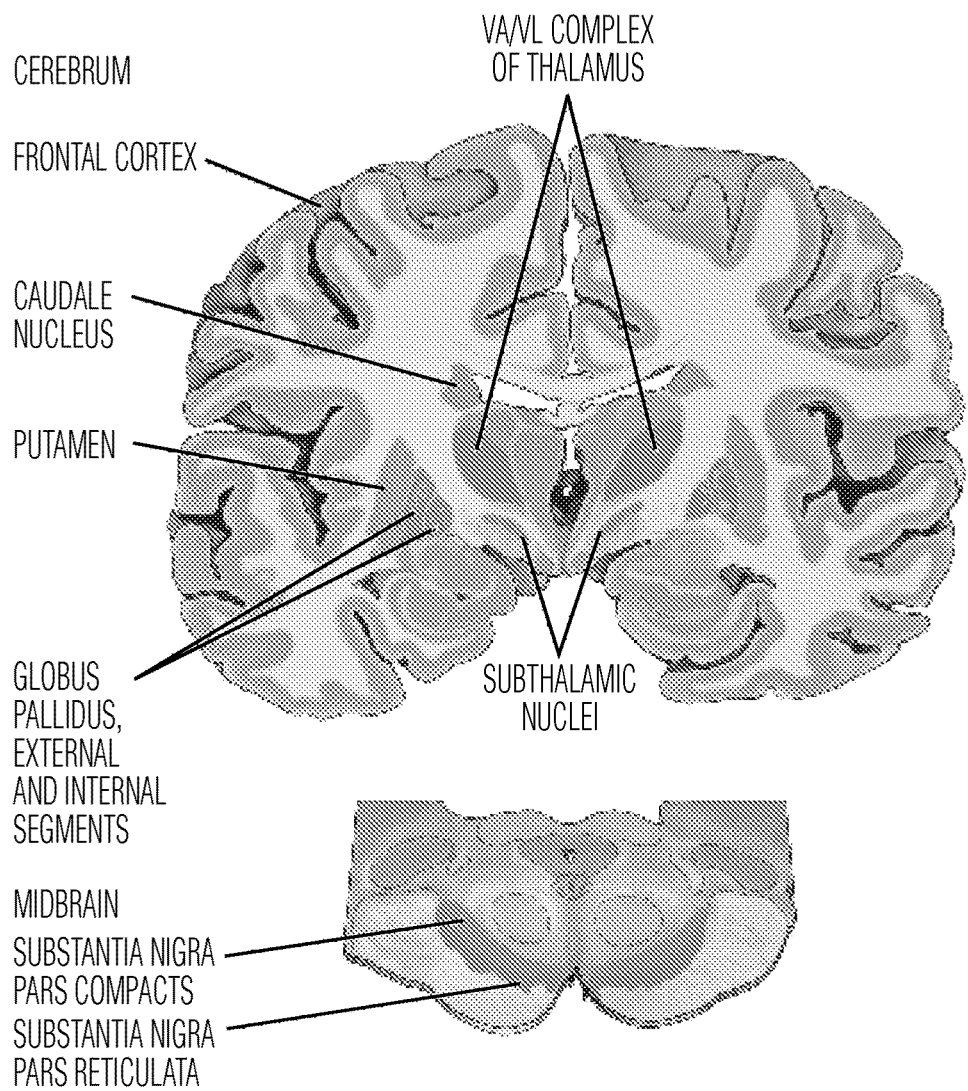
FIG. 1 depicts a schematic coronal section through the brain showing anatomical locations of structures involved in basal ganglia pathways. Targets for HF-DBS in the treatment of Parkinson's disease are the subthalamic nuclei and the globus pallidus internal segments.

High frequency deep brain stimulation (DBS), such as of the thalamus or basal ganglia, is used for the treatment of movement disorders such as Essential Tremors or Parkinson's Disease. FIG. 1 shows a schematic drawing depicting the coronal section of the brain, including anatomical locations of structures involved in basal ganglia pathways.

Figure 2:
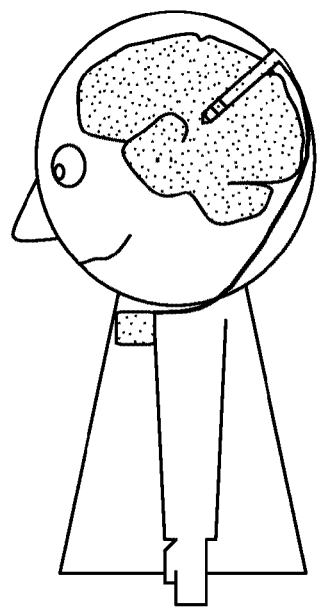
FIG. 2 depicts a schematic layout of a state-of-the-art DBS system consisting of an implanted lead carrying circumferential stimulation electrodes and connected by means of an extension wire to an implanted pulse generator.

A typical electrical brain stimulation system comprises a pulse generator operatively connected to the brain by a lead. The lead has one or more stimulating electrodes at its distal end and is designed to be implanted within the patient's brain so that the system of electrodes is optimally and safely positioned for the desired stimulation of brain tissue at a stimulation target area site. FIG. 2 shows a schematic layout of a state-of-the-art DBS system including implanted stimulation lead having stimulation electrodes or elements, and implanted pulse generator connected thereto.

In a typical DBS procedure the initial step towards effective brain stimulation involves localization or mapping of functional brain structures. Especially when the target is new, in the sense that there is little or no statistical data to identify the target location reliably, it is necessary to determine where within the boundary of the functional target area effective and safe stimulation may be delivered.

Therapeutic benefit and non-desired effects of brain lesioning and chronic neuromodulation depend critically on this localization procedure. This procedure involves three primary steps. First, anatomical localization of brain targets is accomplished using anatomical brain atlases, imaging by means of positive contrast x-rays, CT or MRI under stereotactic conditions. Such standard well known imaging techniques are used to make an initial determination of location coordinates for the target to which the lead will be directed.

Second, electrophysiological identification of functional boundaries between brain structures is carried out by means of single- or multi-cell or multi-recording of characteristic cell discharge patterns. Such a procedure may also be referred to as micro recording or semi-micro recording. Micro recording and semi-micro recording require use of an electrode that is small enough to differentiate between single cell activity or multi-cellular activity, and thus requires a micro-electrode with a very small surface area, e.g. between 1-1000 square micrometers for a semi-micro-electrode and less than one square micrometer for a micro-electrode.

The third step involves electrical test stimulation within the functional brain structures that have been located. Test stimulation of the selected brain structure is necessary to determine: (1) efficacy of stimulation in the identified functional brain structure, and (2) any side effects caused by stimulation of the brain in this area. If the stimulation electrode is too close to the boundary of the identified brain structure the function of adjacent brain structures may be modulated, which in turn can lead to undesired side effects. Test stimulation is clinically most relevant when performed with an electrode or electrodes having a surface area equivalent to that of the chronic implantable electrodes, e.g., in the range of about 1-20 square millimeters.

Currently, after the first step of determining a target location, a lead containing a micro-electrode is placed in the brain to identify functional boundaries with single-cell recording. Then the lead containing the micro-electrode is withdrawn from the brain tissue. After this step, a further step of withdrawing the micro-lead and replacing it with a macro-lead or a third chronic brain stimulation lead may also occur. Those replacements typically require multiple insertions of the leads, all most preferably along the same trajectory path, and therefore increase the risk of intra-cranial hemorrhages with severe permanent disability as a potential consequence. Furthermore, once a lead is positioned and tested to determine that results of stimulation are satisfactory, it is critical that the lead remain in the same place, because even one millimeter of electrode displacement in the wrong direction may cause unsatisfactory results or injury to the brain. Removal of the micro-lead and replacement with one or more other leads also increases the risk that the lead is no longer located in or close enough to the functional target identified by micro recording. Thus it would be desirable to create a lead and a method that is capable of requiring only one implantation of the lead into the patient's brain and facilitates the determination of the stimulation target area and specific stimulation elements and stimulation parameters to enable therapeutic electrical stimulation of the brain tissue.

This is accomplished with the stimulation lead, system and method of providing DBS stimulation using the lead according to the invention disclosed herein. The stimulation lead according to the invention includes an array of one or more stimulation elements and one or more sensing elements located at the distal end of the lead; each of the one or more stimulation elements is capable of providing electrical stimulation to the brain tissue in the target area; and each of the one or more sensing elements is capable of detecting electrical signals produced by nerve cells within the brain. After the first implantation of the lead into the brain along a trajectory that is pre-determined by non-surgical procedures, the array of stimulation and sensing elements is capable of facilitating the location of the target area and the determination for each of the stimulation elements of the required stimulation parameters needed to provide the therapeutic stimulation to the brain tissue in the stimulation target area, without requiring any additional implantations of the lead after the first implantation.

Figure 3:
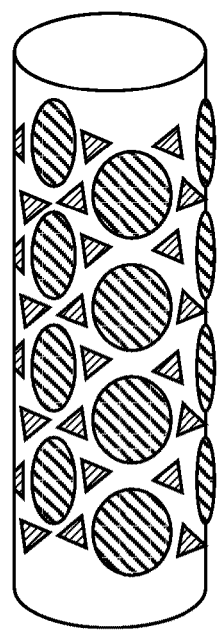
FIG. 3 shows an embodiment of a DBS lead with array of stimulation elements (circles) and sensing elements (triangles).
Figure 4:
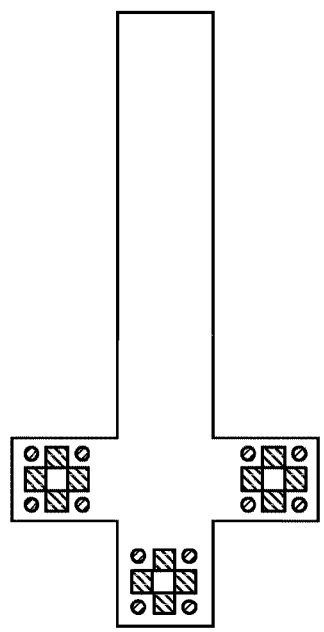
FIG. 4 shows an embodiment of a 3D distribution of stimulation elements (squares) and sensing elements (circles).

The stimulation lead comprises an array of one or more sensing elements and one or more stimulation elements located at the distal or advancing end of the lead during implantation into the brain of a patient, and which will ultimately be in close proximity to the brain tissue to be therapeutically electrically stimulated in the stimulation target area. The array of sensing and stimulations elements can take many geometrical patterns, can be in a three-dimensional distribution about the lead and can be realized by using more than a single lead carrying at least one of the sensing and/or stimulation elements. For example, FIG. 3 shows an embodiment of a DBS lead with an array of stimulation elements (circles) and sensing elements (triangles). FIG. 4 shows an embodiment of 3D distribution of stimulation elements (squares) and sensing elements (circles).

The stimulation elements, in one embodiment of the invention, are metal electrodes. In another embodiment the stimulation elements can be, for example, distributed circumferentially along the lead; for example, in an array along the circumference of the lead.

The sensing elements can also, for example, be distributed circumferentially along the lead; for example, in an array along the circumference of the lead. The sensing elements can be, for example, metal micro-electrodes or capacitative sensing elements. The sensing elements are each independently capable of detecting one or more of electrical signals, action potentials, field potentials, (bio)chemical signals and neurotransmitters. In an embodiment several sensing elements are electrically combined to detect a single electrical signal. In another embodiment the area of a single sensing element is smaller than the area of a single stimulation element.

Figure 5:
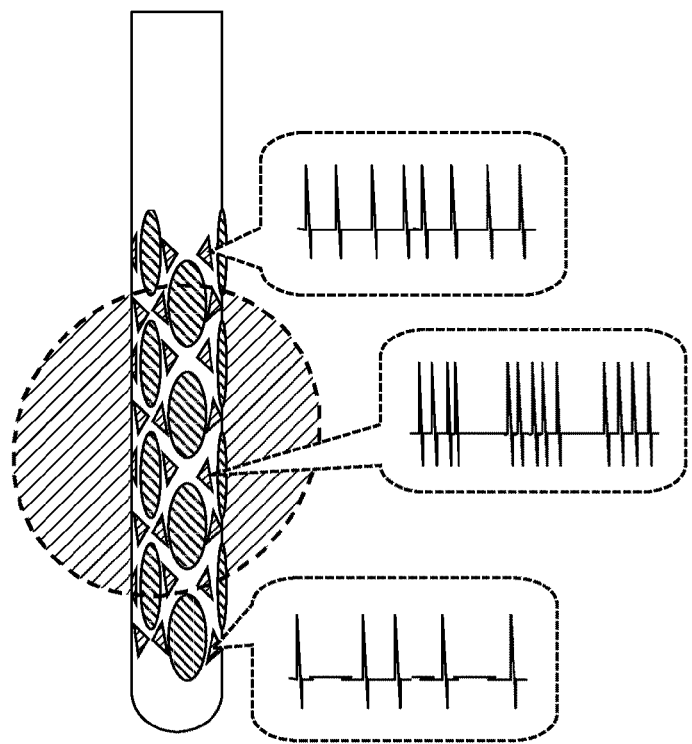
FIG. 5 shows the determination of a stimulation target area based on characteristic signal patterns of brain nerve cells.
Figure 6:
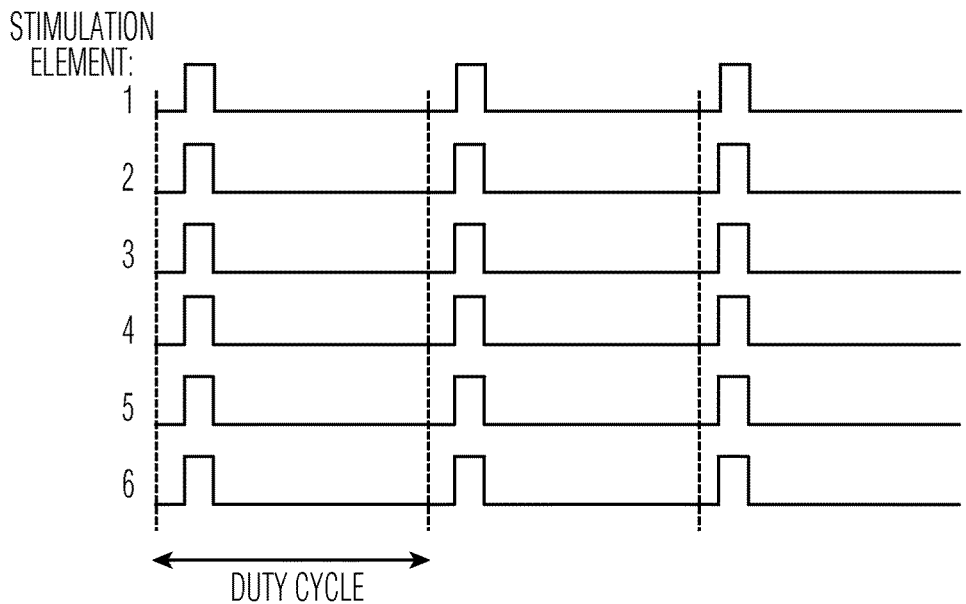
FIG. 6 shows an example of monopolar synchronous stimulation on selected stimulation elements 1-6.
Figure 7:
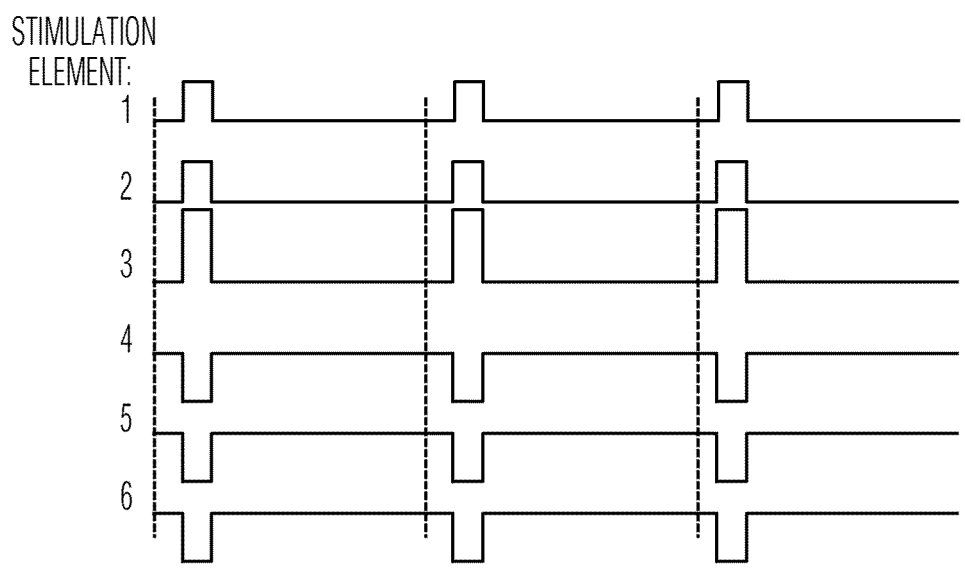
FIG. 7 shows an example of synchronous stimulation with amplitude- and polarity-mediated stimulation field steering on selected stimulation elements 1-6.
Figure 8:
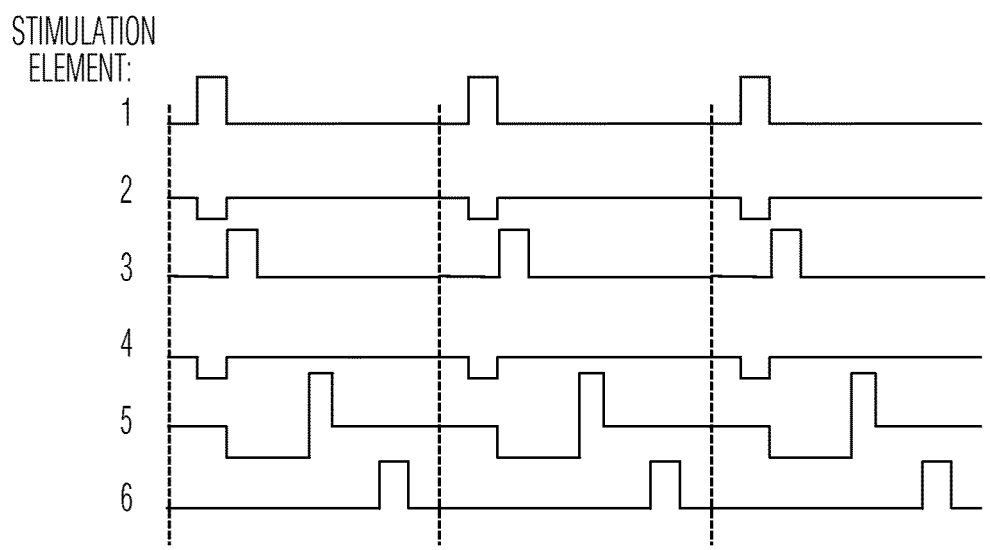
FIG. 8 shows an example of complex stimulation patterns on selected stimulation elements 1-6.

The detected information provided by the sensing elements, such as the electric signals or other signals abovementioned produced by the brain nerve cells, is utilized by a controller or processing unit in communication with the sensing and stimulating elements to facilitate the spatial location and boundary of the stimulation target area in the brain, as is shown in FIG. 5. Also, such detected information facilitates the determination of which specific stimulating elements will be used in providing therapeutical electrical stimulation to the brain tissue in the stimulation target area, as well as the stimulation parameters that will be used for each stimulation element. Such stimulation parameters include, for example, one or more of stimulation amplitude, polarity, duration repetition frequency, waveform, and relative phase within the stimulation duty cycle. FIGS. 6-8 show, for example, several possible stimulation patterns for stimulation elements identified as numbers 1-6.

The controller or processing unit can be utilized for one or more functions, such as, for processing signal data, receiving signal data, transmitting signal data or new commands; communicating with a technician or physician or other component of the lead system, such as one or more of the sensing and/or stimulating elements, external processors, computers, viewing monitors, etc. Thus, for example, the controller may be integrated in the probe or DBS unit. Alternatively, the controller may be located externally to the DBS lead or system, for example at a workstation, to carry out the extensive computations needed for practicing the method of DBS stimulation, including stimulation target area determination. Also, the brain signals obtained by the one or more sensing elements may, for example, be presented in viewable form, for example graphically, to a user (for example, a physician) to enable the user, possibly with the help of computer-analysis/processing of the signal/data to make initial suggestions for the optimum stimulation target area and placement of the DBS lead for stimulation. This latter approach most closely corresponds to current best practice; namely, the neurophysiologist determines the target position for the DBS lead based on sensed signals.

In an embodiment the stimulation elements are directly associated with the sensing elements. The association is based on a geometric relation between the position of the sensing and stimulation elements. For example, each stimulation element may be associated with a single sensing element or combination of sensing elements; or each stimulation element can be associated with another unique sensing element, for example, a sensing element for detecting one type of electric signal; or the number of sensing elements is larger than the number of stimulation elements. When the number of sensing elements is greater than the number of stimulating elements, a "center of gravity" approach may be used to associate the sensing and stimulating elements; for example, if multiple sensing elements surrounding a stimulation element pick up the correct signals, this stimulation element may be presumed to lie in the target area for stimulation. The sensing elements may, for example, pick up firing patterns of neurons and use the characteristics of these signals to discriminate between different brain regions. Alternatively, the sensing elements may also measure local impedance to discriminate between gray and white matter and thus obtain additional information about local neuro-anatomy in the surrounding of the probe. By combining multiple measurement types the discrimination between different tissue types, anatomical/functional structures, etc., will become more accurate. In another embodiment field steering techniques are employed to finely position the target stimulation area or field. In another embodiment relative stimulation amplitudes and/or timings of stimulating elements are associated with sensing elements. Also, the detected signal information by the sensing elements can be read out in parallel or sequentially.

The stimulation lead can be incorporated into a stimulation system for providing after implantation therapeutic electrical stimulation in a stimulation target area of the brain of a patient. Such a system includes a pulse generator for generating and transmitting electrical pulses required for stimulation to the stimulating elements.

In another embodiment of the invention, a method of providing therapeutic deep brain electrical stimulation to tissue in a stimulation target area of a patient's brain is disclosed comprising determining by non-surgical imaging procedures the approximate target area for stimulation and the trajectory for implantation of a deep brain stimulation lead into the approximate target area; implanting along the trajectory and into the approximate target area the deep brain stimulation lead, the above disclosed stimulation lead; detecting by the one or more sensing elements of the electrical signals produced by nerve cells within the brain; determining from the detected electrical signals produced by nerve cells within the brain the three dimensional spatial location and boundary of the stimulation target area within the approximate target area; determining which of the one or more specific stimulation elements will be used to provide stimulation to the brain tissue within the stimulation target area and the specific stimulation parameters for each of the one or more stimulation elements to be used during the stimulation; and performing stimulation of the tissue within the stimulation target area of the brain with the specific stimulation elements using the specific stimulation parameters for each of the specific stimulation elements.

Another embodiment provides that the detecting by the one or more sensing elements of the electrical signals produced by nerve cells within the brain, further comprises reading out the electrical signal characteristics of the nerve cells within the brain detected by the one or more sensing elements; and determining the specific sensing elements that detect the signal characteristics that correspond to the stimulation target area.

Another embodiment provides a method further comprising prior to the step of performing the stimulation of the brain tissue, testing the stimulation target area by delivering test electrical stimulation by the specific one or more stimulation elements to the brain tissue in the stimulation target area and repeating the steps of the method as needed until confirmation of a functionally efficient stimulation target area is obtained.

In another embodiment, there is provided a method for "first-time-right-placement" of a DBS lead. This is achieved by using the stimulation lead according to the invention carrying an array of stimulation elements and an integrated array of sensing elements. The method consists of the following steps:

1. implanting the novel DBS lead along the trajectory as determined by stereotactic imaging procedures (and/or other surgery planning tool) well within the approximate target area of the brain where the stimulation target area for the tissue to be stimulated should be located.

2. reading out the signal characteristics detected by the various sensing elements integrated in the DBS lead.

3. determining the sensing elements that detect the signal characteristics corresponding to the intended stimulation target area.

4. associating with the sensing elements that detect the signal characteristics corresponding to the intended stimulation target area the spatial location and boundary extent of the stimulation target area.

5. associating with the derived spatial location of the stimulation target a shape of the required stimulation field needed to cover the stimulation target area.

6. associating with the required stimulation field a group of specific stimulation elements.

7. optionally testing the so identified intended stimulation target area by delivering test stimulation using the group of specific stimulation elements, and optionally repeating steps 2 to 7 until confirmation of a functionally efficient stimulation target area is obtained;
   a. further optionally using available additional diagnostic tools to support targeting, e.g. intra-operative functional imaging, fused imaging, etc.

8. determining for each of the specific stimulation elements the required stimulation parameters like stimulation amplitude, polarity, duration, repetition frequency, waveform, and relative phase within the stimulation duty cycle.

9. performing stimulation on the brain tissue in the stimulation target area with the associated specific stimulation elements according to the derived stimulation parameters.

While the present invention has been described with respect to specific embodiments thereof, it will be recognized by those of ordinary skill in the art that many modifications, enhancements, and/or changes can be achieved without departing from the spirit and scope of the invention. Therefore, it is manifestly intended that the invention be limited only by the scope of the claims and equivalents thereof.

The invention claimed is:

1. A stimulation lead having a distal end for providing therapeutic electrical stimulation to tissue in a target area, the lead comprising:
   an array of a plurality of stimulation elements and a plurality of sensing elements located at the distal end of the lead, the array including columns of two or more of the plurality of stimulation elements, the columns extending down a longitudinal length of the stimulation lead and spaced from one another around the circumference of the stimulation lead, at least one of the plurality of stimulation elements being adjacent to and surrounded by two or more of the plurality of sensing elements, each of the plurality of sensing elements configured to detect electrical signals, at least one of the plurality of sensing elements being positioned between two or more of the plurality of stimulation elements, a number of the plurality of sensing elements being greater than a number of the plurality of stimulation elements, the plurality of sensing elements comprising a plurality of sets of sensing elements, each of the sets of sensing elements comprising two or more sensing elements, each of the plurality of stimulation elements being directly associated with one of the sets of sensing elements, the association being based on a geometric relation between which sets of sensing elements surround which ones of the plurality of stimulation elements, and each set of sensing elements is associated with only one stimulation element that is surrounded by respective set of sensing elements; and
   a controller configured to receive signals from one or more of the plurality of sensing elements, derive a spatial location and boundary of the target area based on locations of the sensing elements that sensed the signal, and determine that one or more of the plurality of stimulation elements that are surrounded by the respective sets of the sensing elements whose sensing elements sensed the signal lie in the target area and should provide the therapeutic electrical stimulation that covers the spatial location and the boundary of the target area, and control delivery of the therapeutic electrical stimulation via the determined stimulation elements.

2. The stimulation lead of claim 1, wherein the plurality of stimulation elements are metal electrodes.

3. The stimulation lead of claim 1, wherein the plurality of sensing elements are metal microelectrodes or capacitive sensing elements.

4. The stimulation lead of claim 1, wherein the plurality of stimulation elements and the plurality of sensing elements are distributed in an array circumferentially on the surface of the lead.

5. The stimulation lead of claim 1, wherein the plurality of sensing elements are each individually capable of detecting one or more of electrical signals, action potentials, field potentials, biochemical signals and neurotransmitters.

6. The stimulation lead of claim 1, wherein the area of one of the plurality of sensing elements is smaller than the area of two of the plurality of stimulation elements.

7. The stimulation lead of claim 1, wherein the plurality of sensing elements are electrically combined to detect a single electrical signal.

8. The stimulation lead of claim 1, wherein the stimulation parameters are selected from one or more of stimulation amplitude, polarity, duration repetition frequency, waveform, and relative phase within the stimulation duty cycle.

9. The stimulation lead of claim 1, wherein the controller is configured to determine required stimulation parameters needed for the therapeutic electrical stimulation for each of the plurality of stimulation elements associated with the sensing elements that sensed the signal.

10. The stimulation lead of claim 1, wherein the controller is configured to use the signals received from one or more of the plurality of sensing elements to control relative stimulation amplitudes and/or timings of each of the plurality of stimulation elements associated with the sets of sensing elements that sensed the signal.

11. The stimulation lead of claim 1, wherein a set of the sensing elements comprises six sensing elements adjacent to and spaced around only one of the plurality of stimulation elements with which the set of sensing elements is associated.

12. The stimulation lead of claim 1, wherein the at least one of the plurality of sensing elements is positioned between three of the plurality of stimulation elements.

\* \* \* \* \*